United States Patent
Wei

[11] Patent Number: 6,022,314
[45] Date of Patent: Feb. 8, 2000

[54] METHOD FOR AUTOMATED DISPLAY OF DATE AND TIME SPECIFIC BIORHYTHMIC ACUPUNCTURE POINTS

[76] Inventor: Chih-Shing Wei, 3 Mindy Ct., Lattingtown, N.Y. 11560

[21] Appl. No.: 08/628,558

[22] Filed: Apr. 10, 1996

[51] Int. Cl.[7] .................................................. A01B 5/00
[52] U.S. Cl. ......................... 600/300; 600/548; 368/327
[58] Field of Search ................................. 128/630, 733, 128/734, 738; 368/327; 600/547–548

[56] References Cited

U.S. PATENT DOCUMENTS

| | | | |
|---|---|---|---|
| 4,016,870 | 4/1977 | Lock | 128/2.1 C |
| 4,303,996 | 12/1981 | Schmitz | 386/82 |
| 4,408,617 | 10/1983 | Auguste | 128/735 |
| 4,712,923 | 12/1987 | Martin | 368/10 |
| 5,208,790 | 5/1993 | Sato | 368/15 |
| 5,366,379 | 11/1994 | Yang et al. | 434/365 |
| 5,366,483 | 11/1994 | Sadkhin | 607/3 |
| 5,515,344 | 5/1996 | Ng | 128/738 |
| 5,592,605 | 1/1997 | Asuma et al. | 395/348 |

OTHER PUBLICATIONS

"Clinical Research of Acupuncture Point Selection Based on the Midday–Midday Energy Flux Principle of Date & Time Specific Acupuncture Points" Li et al, China 1987 (ISBN 957–624–298–3).

Campbell, S. et al "Extra Occular Circadion Phototransduction in Humans" Science vol. 279 Jan. 16, 1998.

The New Encyclopedia Britannica, Macropedia vol. 3, pp. 608–609, by Encyclopedia Britannica, Inc., 1976.

Manaka and Urquhart, The Layman's Guide to Acupuncture, pp. 77–81, by Weatherhill, Inc., New York, 1991.

Ding, Acupuncture, Meridian Theory, and Acupuncture Points, pp. 139–140, by China Books & Periodicals, Inc., San Francisco, California, 1992.

*Primary Examiner*—Francis J. Jaworski

[57] ABSTRACT

A method for operating an electronic apparatus so as to produce an automated display of date and time specific biorhythmic acupuncture points is disclosed. The method monitors a current Gregorian-calendar date and time generated by the electronic apparatus, converts it into a Chinese-calendar Kan-day and Chih-period index affiliated with a biorhythm, utilizes the index to indicate and retrieve a biorhythmic acupuncture point from a table of predetermined biorhythmic acupuncture points, and displays the retrieved biorhythmic acupuncture point and current date and time. Once started, the method continues to display and update current date and time and their corresponding biorhythmic acupuncture point until it is interrupted by a user of the electronic apparatus.

5 Claims, 5 Drawing Sheets

|  | Kan-day 1 | Kan-day 2 | Kan-day 3 | Kan-day 4 | Kan-day 5 |
|---|---|---|---|---|---|
| Chih-period 1 | GB-38 Yangfu (Lateral Support) | SI-2 Qiangu (Foremost Valley) | ST-36 Zusanli (Foot Three Cun) | LI-3 Sanjian (Third Interval) | SJ-1 Guanchong (Rushing Passage) |
| Chih-period 2 | LR-2 Xingjian (Walk Between) | HT-3 Shaohai (Young Sea) | SP-3 Taibai (Great White) | PC-3 Quze (Curved Swamp) | KI-7 Fuliu (Stay Hidden) |
| Chih-period 3 | SI-8 Xiaohai (Small Sea) | ST-43 Xiangu (Sinking Valley) | SJ-10 Tianjing (Celestial Well) | BL-60 Kunlun (Prominence) | LU-5 Chize (Narrow Swamp) |
| Chih-period 4 | HT-7 Shenmen (Spiritual Gate) | PC-5 Jianshi (Intermediary) | LU-8 Jingqu (Meridian Passage) | LI-2 Erjian (Second Interval) | LR-8 Ququan (Curved Spring) |
| Chih-period 5 | SJ-6 Zhigou (Limb Trench) | LI-5 Yangxi (Yang Stream) | ST-45 Lidui (Strict Door) | GB-34 Yanglingquan (Lateral Mound Spring) | ST-45 Lidui (Strict Door) |
| Chih-period 6 | SP-5 Shangqiu (Merchant Hill) | SP-5 Shangqiu (Merchant Hill) | KI-10 Yingu (Yin Valley) | SP-5 Shangqiu (Merchant Hill) | PC-7 Daling (Large Mound) |
| Chih-period 7 | HT-7 Shenmen (Spiritual Gate) | BL-40 Weizhong (Knee Center) | HT-7 Shenmen (Spiritual Gate) | SJ-3 Zhongzhu-Hand (Middle Islet) | ST-45 Lidui (Strict Door) |
| Chih-period 8 | LU-5 Chize (Narrow Swamp) | SI-8 Xiaohai (Small Sea) | PC-8 Laogong (Labor Palace) | HT-9 Shaochong (Small Rush) | SI-8 Xiaohai (Small Sea) |
| Chih-period 9 | BL-65 Shugu (Restrict Bone) | SJ-2 Yemen (Fluid Gate) | SI-1 Shaoze (Small Swamp) | ST-41 Jiexi (Open Stream) | LI-2 Erjian (Second Interval) |
| Chih-period 10 | PC-9 Zhongchong (Medium Rush) | LR-1 Dadun (Large Mound) | HT-4 Lingdao (Spirit Passage) | SP-2 Dadu (Large Prominence) | KI-1 Yongquan (Gushing Spring) |
| Chih-period 11 | GB-44 Zuqiaoyin (Foot Yin Cavity) | SI-5 Yanggu (Yang Valley) | ST-44 Neiting (Inner Court) | LI-11 Quchi (Curved Pond) | BL-65 Shugu (Restrict Bone) |
| Chih-period 12 | LR-4 Zhongfeng (Middle Border) | HT-8 Shaofu (Young Prefecture) | KI-10 Yingu (Yin Valley) | LU-9 Taiyuan (Great Pond) | KI-1 Yongquan (Gushing Spring) |

FIG. 3A

|  | Kan-day 6 | Kan-day 7 | Kan-day 8 | Kan-day 9 | Kan-day 10 |
|---|---|---|---|---|---|
| Chih-period 1 | GB-38 Yangfu (Lateral Support) | SI-2 Qiangu (Foremost Valley) | ST-36 Zusanli (Foot Three Cun) | LI-3 Sanjian (Third Interval) | SJ-1 Guanchong (Rushing Passage) |
| Chih-period 2 | LR-2 Xingjian (Walk Between) | HT-3 Shaohai (Young Sea) | SP-3 Taibai (Great White) | PC-3 Quze (Curved Swamp) | KI-7 Fuliu (Stay Hidden) |
| Chih-period 3 | SI-8 Xiaohai (Small Sea) | ST-43 Xiangu (Sinking Valley) | SJ-10 Tianjing (Celestial Well) | BL-67 Zhiyin (Reaching Yin) | LU-5 Chize (Narrow Swamp) |
| Chih-period 4 | HT-7 Shenmen (Spiritual Gate) | PC-5 Jianshi (Intermediary) | LU-11 Shaoshang (Young Merchant) | LI-2 Erjian (Second Interval) | LR-8 Ququan (Curved Spring) |
| Chih-period 5 | SJ-6 Zhigou (Limb Trench) | LI-1 Shangyang (Merchant Yang) | ST-45 Lidui (Strict Door) | GB-43 Xiaxi (Narrow Stream) | ST-45 Lidui (Strict Door) |
| Chih-period 6 | SP-1 Yinbai (Hidden White) | SP-5 Shangqiu (Merchant Hill) | KI-2 Rangu (Navicular Bone) | SP-5 Shangqiu (Merchant Hill) | PC-7 Daling (Large Mound) |
| Chih-period 7 | HT-7 Shenmen (Spiritual Gate) | BL-66 Zutonggu (Foot Passage Valley) | HT-7 Shenmen (Spiritual Gate) | SI-3 Houxi (Rear Stream) | ST-45 Lidui (Strict Door) |
| Chih-period 8 | LU-10 Yuji (Fish Junction) | SI-8 Xiaohai (Small Sea) | LU-9 Taiyuan (Great Pond) | HT-9 Shaochong (Small Rush) | SI-8 Xiaohai (Small Sea) |
| Chih-period 9 | BL-65 Shugu (Restrict Bone) | GB-41 Zulinqi (Foot Control Tear) | SI-1 Shaoze (Small Swamp) | ST-41 Jiexi (Open Stream) | LI-2 Erjian (Second Interval) |
| Chih-period 10 | KI-3 Taixi (Great Stream) | LR-1 Dadun (Large Mound) | HT-4 Lingdao (Spirit Passage) | SP-2 Dadu (Large Prominence) | KI-1 Yongquan (Gushing Spring) |
| Chih-period 11 | GB-44 Zuqiaoyin (Foot Yin Cavity) | SI-5 Yanggu (Yang Valley) | ST-44 Neiting (Inner Court) | LI-11 Quchi (Curved Pond) | BL-65 Shugu (Restrict Bone) |
| Chih-period 12 | LR-4 Zhongfeng (Middle Border) | HT-8 Shaofu (Young Prefecture) | SP-9 Yinlingquan (Yin Mound Spring) | LU-9 Taiyuan (Great Pond) | KI-1 Yongquan (Gushing Spring) |

FIG. 3B

DATE: 1995 DEC 16
TIME: 03:25 PM
POINT: SI-1 Shaoze
(Small Swamp)

METHOD FOR AUTOMATED DISPLAY OF DATE AND TIME SPECIFIC BIORHYTHMIC ACUPUNCTURE POINTS

FIELD OF THE INVENTION

This invention relates in general to methods for operating electronic apparatus, in particular to a method for operating an electronic apparatus so as to produce an automated display of date and time specific biorhythmic acupuncture points.

BACKGROUND OF THE INVENTION

It is well established in the fields of acupuncture and acupressure that a human body has date and time specific biorhythmic acupuncture points which can be identified according to a certain biorhythmic or biological clock within the human body. These biorhythmic acupuncture points are part of the commonly recognized acupuncture points. When active, these biorhythmic acupuncture points are more sensitive or responsive to the application of acupuncture needles or massaging pressure than other non-active acupuncture points. A so-called date and time specific biorhythmic acupuncture point is an acupuncture point which is active at a particular time in a particular day of a particular month of a particular year. When a human subject travels across time zones, the biorhythmic clock within the human subject's body often requires only an acclimatization period to adapt itself to a new time zone's biological environment as defined by the sun, the moon, and the earth. Thus such changes of time zone are usually not considered in identifying date and time specific biorhythmic acupuncture points, only localized date and time need to be considered.

The names and anatomical locations of all commonly recognized acupuncture points on so-called meridians are well established and standardized. Identifying and locating specific acupuncture points is a prerequisite to the application of acupuncture or acupressure. U.S. Pat. No. 4,016,870 to Lock (1977) and U.S. Pat. No. 4,408,617 to Auguste (1983) disclose two devices for measuring and detecting general acupuncture points; however, both devices are not intended to identify specific acupuncture points that are biorhythmic. U.S. Pat. No. 5,366,379 to Yang and Kim (1994) discloses a device for identifying acupuncture points on fingers based on symptom reference codes specified by a user of the device, but the device is not intended to identify specific biorhythmic acupuncture points.

Knowledge of biorhythmic acupuncture points helps one to identify and locate specific acupuncture points, on a human subject's skin, governed by an underlying biorhythm, for the purpose of either inserting acupuncture needles or applying pressure at such locations to induce preferred therapeutic effects. U.S. Pat. No. 5,366,483 to Sadkhin (1994) discloses a device for treating biologically active acupuncture points on a patent's skin; however, this device is not intended to automatically identify specific biorhythmic acupuncture points.

It is certain that a display device capable of monitoring current date and time, and depicting automatically a set of commonly used, date and time specific biorhythmic acupuncture points is novel and will facilitate the task of those interested in the practice of acupuncture or acupressure in identifying biorhythmic acupuncture points.

There exist many electronic schedulers or organizers which can display current date and time and their specific calendar and personal information or messages. A digital watch which allows a watch user to program and display both horological and alphanumeric message information is disclosed in U.S. Pat. No. 4,303,996 to Schmitz (1981). An electronic calendar device which keeps time and displays preprogrammed calendar information and user programmed personal messages is disclosed in U.S. Pat. No. 4,712,923 to Martin (1987). These two and other existing electronic schedulers or organizers do not provide means for automatically displaying date and time specific biorhythmic acupuncture points. An astronomical data indicating device which calculates and displays precise astronomical data based on date, time, and a user's location on the earth is disclosed in U.S. Pat. No. 5,208,790 to Sato (1993). This device is not intended to automatically identify biorhythmic acupuncture points which become active at specific dates and times.

OBJECTS OF THE INVENTION

An object of the present invention is to provide a method for producing an automated display of names of date and time specific biorhythmic acupuncture points.

Another object of the present invention is to provide a method for producing an automated display of textual descriptions of names and locations of date and time specific biorhythmic acupuncture points.

Yet another object of the present invention is to provide a method for producing an automated display of pictorial descriptions of names and locations of date and time specific biorhythmic acupuncture points.

These and other objects of the present invention will become apparent from a consideration of the ensuing description and drawings.

BRIEF DESCRIPTION OF THE DRAWING FIGURES

FIG. 3A is the first half of a table of 120 biorhythmic acupuncture points listed according to their respective Kan-day and Chih-period indices.

FIG. 3B is the second half of a table of 120 biorhythmic acupuncture points listed according to their respective Kan-day and Chih-period indices.

SUMMARY OF THE INVENTION

Figure 1:
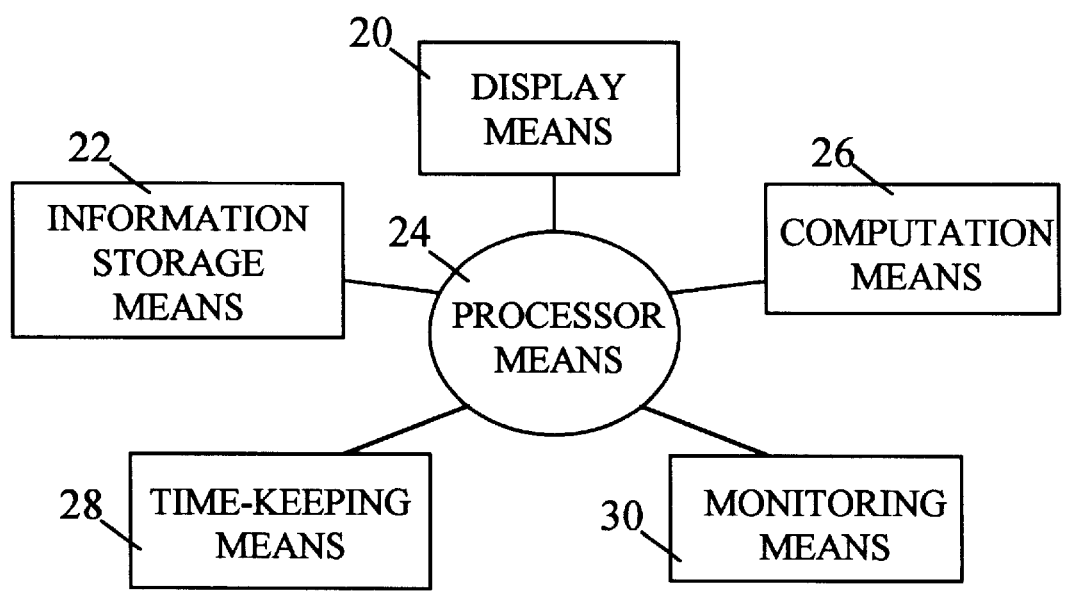
FIG. 1 is a block diagram illustrating a set of functional elements of an electronic apparatus operated by a preferred embodiment of the present invention.

The present invention comprises a method for operating an electronic apparatus so as to produce an automated display of date and time specific biorhythmic acupuncture points. The method monitors a current Gregorian-calendar date and time generated by the electronic apparatus, converts it into a Chinese-calendar Kan-day and Chih-period index affiliated with a biorhythm, utilizes the index to indicate and retrieve a biorhythmic acupuncture point from a table of predetermined biorhythmic acupuncture points, and displays the retrieved biorhythmic acupuncture point and current date and time. Once started, the method continues to display and update current date and time and their corresponding biorhythmic acupuncture point until it is interrupted by a user of the electronic apparatus.

DESCRIPTION OF PREFERRED EMBODIMENT

A preferred embodiment of the present invention is a method for producing an automated display of names of date and time specific biorhythmic acupuncture points. A name of a biorhythmic acupuncture point is considered as a biorhythmic indicator governed by an underlying biorhythm. An essential element of the embodiment is the conversion of a Gregorian-calendar date and time into a Kan-day and Chih-period index based on the Chinese lunar-solar calendar. A date and time is considered as a temporal datum consisting of values of specific year, month, day, hour, minute, and second; and a Kan-day and Chih-period index is considered as a biorhythm-based indexing means consisting of a Kan-day value and a Chih-period value. A detailed description of a procedure for converting a date and time into a Kan-day and Chih-period index is given in the following paragraph.

Many practitioners of the traditional Chinese medicine believe that there is a vital force or energy circulating through a human body in a ten-day cycle at a speed which is in sync with the Chinese lunar-solar calendar and its Kan-Chih based day and hour count system. The ten-day cycle consists of ten so-called Kan-days which cycle continuously through the Chinese lunar-solar calendar. The use of Kan-days in counting days in the Chinese lunar-solar calendar is similar to the use of the seven week days, Sunday through Saturday, in counting days in the Gregorian calendar. It is a known fact that the first day of year 1984 in the Gregorian calendar is a first Kan-day or Kan-day 1 in the Chinese lunar-solar calendar. This enables the conversion of any day in any year after the first day of year 1984 into a corresponding Kan-day, by calculating its total number of days elapsed since the first day of year 1984 and incrementing the rightmost digit of the resultant number to arrive at its corresponding Kan-day. For example, the Gregorian-calendar date "1984 February 1" has 31 elapsed days since the first day of year 1984, and the rightmost digit "1" indicates that it is a second Kan-day or Kan-day 2. Similarly, the Gregorian-calendar date "1995 December 16" has 4367 elapsed days since the first day of year 1984, and the rightmost digit "7" indicates that it is an eighth Kan-day or Kan-day 8. A rightmost digit "0" would indicate a first Kan-day or Kan-day 1, and a rightmost digit "9" would indicate a tenth Kan-day or Kan-day 10. The Chinese Kan-Chih day and hour count system divides the 24-hour period of each day into 12 two-hour Chih-periods. The two-hour period from 11:00 PM of the preceding day to 12:59 AM of the current day is commonly designated as a first Chih-period or Chih-period 1 of the current day, the period from 1:00 AM to 2:59 AM is a second Chih-period or Chih-period 2. The other ten Chih-periods are designated accordingly, and the period from 9:00 PM to 10:59 PM is a twelfth Chih-period or Chih-period 12. According to these designations, the time "03:25 PM" will fall within and be converted into a ninth Chih-period or Chih-period 9. It is also believed that this circulating body energy reaches a particular acupuncture point at a particular Chih-period of a particular Kan-day within the ten-day cycle, thus signaling that this particular acupuncture point will become and remain active during this particular two-hour period. This results in the human body energy circulating through a set of 120 commonly used, known biorhythmic acupuncture points every ten days. The name of the biorhythmic acupuncture point indicated by a particular date and time of the Gregorian calendar can be obtained by first converting the date and time into a corresponding Kan-day and Chih-period index, then using the index to indicate and retrieve the name from a table of the names of the 120 predetermined biorhythmic acupuncture points. The contents of this table will be described later.

In this embodiment, a date and time is considered as a temporal datum, a ten-day period starting with a Kan-day 1 is considered as a biorhythmic period, and a Kan-day and Chih-period index is considered as a biorhythm-based indexing means. Although other sets of biorhythmic acupuncture points have also been used in acupuncture and acupressure which entail their distinctive sets of temporal datum, biorhythmic period, and biorhythm-based indexing means, the procedure described herein for mapping a temporal datum to a biorhythmic acupuncture point is applicable to all such practices.

The method of this embodiment takes the form of an application program, which can be used to operate an electronic apparatus equipped with a display panel or screen. The manner in which the application program produces an automated display of names of date and time specific biorhythmic acupuncture points can be understood by examining a block diagram of a set of functional elements of such an electronic apparatus, shown in FIG. 1, and a flowchart of a set of operational steps of the application program, shown in FIG. 2. It will be apparent to those skilled in the art of computer programming that such an application program can be manufactured, following the operational steps illustrated in FIG. 2, to operate an electronic apparatus equipped with a display panel, such as a computer or electronic organizer, so as to produce the display effects described herein.

Figure 2:
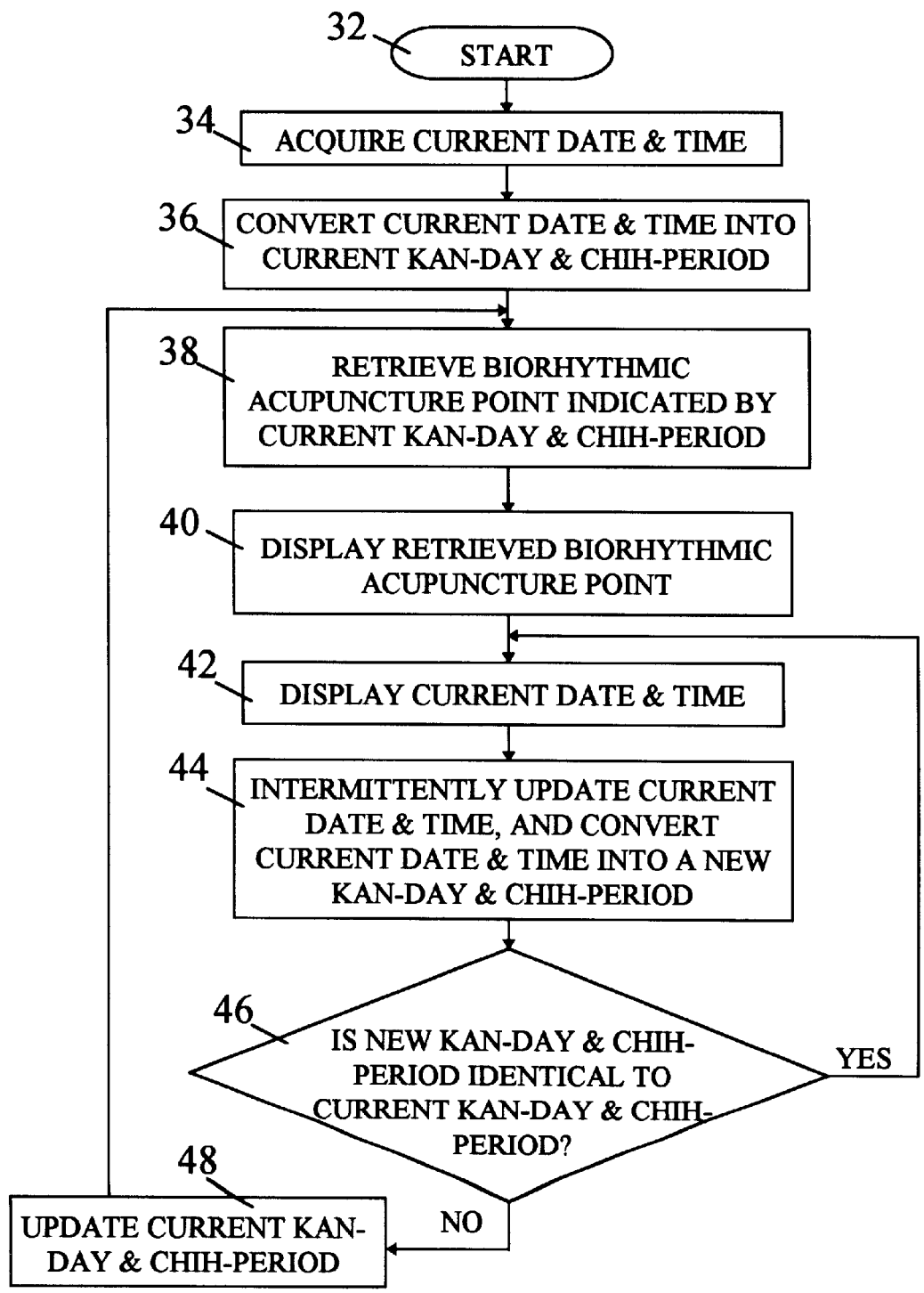
FIG. 2 is a flowchart illustrating a set of operational steps of the preferred embodiment of the present invention.

The application program is coded so as to direct a processor means 24, shown in FIG. 1, to execute steps 32 through 48 as shown in FIG. 2. The application program is usually started by a user of the electronic apparatus, as illustrated in step 32. In step 34, the application program acquires a current date and time from a time-keeping means 28. The continuous operation of time-keeping means 28 in maintaining correct date and time counts is provided by the electronic apparatus and is independent of the state of the application program, which can be started or terminated at any date and time. Once started, the application program can be interrupted or terminated by an explicit action taken by a user of the apparatus such as switching to another application program or shutting off the apparatus without disrupting the operation of time-keeping means 28. Then, in step 36, the application program converts the current date and time into a current Kan-day and Chih-period index using a computation means 26. A detailed description of this computation means has been given in the second paragraph of this section. In the case that an acquired date and time incorporates a certain artificially defined time zone adjustment, such as a daylight-saving time, computation means 26 can either be made to accept the adjustment and take no additional action since the biorhythmic clock within a human subject often fine-tunes itself to adapt to such an adjustment, or be modified such that it recovers a pre-adjusted date and time from an acquired date and time before performing the conversion.

In step 38, the application program then retrieves the name of the active biorhythmic acupuncture point indicated by the current Kan-day and Chih-period index from a table of names of 120 biorhythmic acupuncture points stored in an information storage means 22. The origin of this table has been described in the second paragraph of this section. The complete table is shown in FIGS. 3A and 3B as two separate tables, and is arranged according to the allowed ten Kan-days and twelve Chih-periods. A set of widely recognized symbols for acupuncture points is used in FIGS. 3A and 3B.

All of the 120 acupuncture points listed are located on the so-called twelve regular meridians, which are related to specific organs and are known as meridians Lung (LU), Large Intestine (LI), Stomach (ST), Spleen (SP), Heart (HT), Small Intestine (SI), Urinary Bladder (BL), Kidney (KI), Pericardium (PC), Sanjiao (SJ), Gallbladder (GB), and Liver (LR). Thus the GB-38 symbol indicated by Kan-day 1 and Chih-period 1, as shown in FIG. 3A, represents the 38th acupuncture point on the Gallbladder meridian. The rest of the GB-38 entry in the table in FIG. 3A provides a standardized Chinese name of the acupuncture point, together with a parenthesized English interpretation of the Chinese name. Hence the GB-38 acupuncture point is known as Yangfu (Lateral Support). In the complete table shown in FIGS. 3A and 3B, a name of an acupuncture point comprises its symbol, Chinese name, and English interpretation. It is evident that other combinations of terms can be used to denote an acupuncture point, and that certain acupuncture points in the complete table shown in FIGS. 3A and 3B are indicated by more than one Kan-day and Chih-period index.

After retrieving the name of the indicated biorhythmic acupuncture point, the application program depicts the name on a display means 20, as illustrated in step 40. The application program then depicts the current date and time on display means 20, as illustrated in step 42. It then executes a monitoring means 30 to monitor changing date and time data generated by time-keeping means 28 by acquiring a new date and time intermittently at a predetermined frequency, equating the current date and time with the new date and time, and converting the current date and time into a new Kan-day and Chih-period index utilizing computation means 26. These monitoring actions are also indicated in step 44, and the frequency at which the application program monitors changing date and time data can be set at once every second or at a specific frequency imposed by the processing speed of processor means 24. The application program then compares the current Kan-day and Chih-period index with the new Kan-day and Chih-period index. This action is indicated in step 46. When it is found that the current Kan-day and Chih-period index is identical to the new Kan-day and Chih-period index, the application program branches to step 42 to display the updated current date and time. This branching action is indicated in the YES-branch in step 46. Otherwise, the application program follows the NO-branch in step 46 to step 48, in which the current Kan-day and Chih-period index is equated with the new Kan-day and Chih-period index. It then continues to step 38 to retrieve the name of another biorhythmic acupuncture point. Thus the application program of this embodiment will continue to produce an automated display of current date and time and their corresponding biorhythmic acupuncture point until it is explicitly interrupted by a user of the apparatus.

Figures 4, 5:
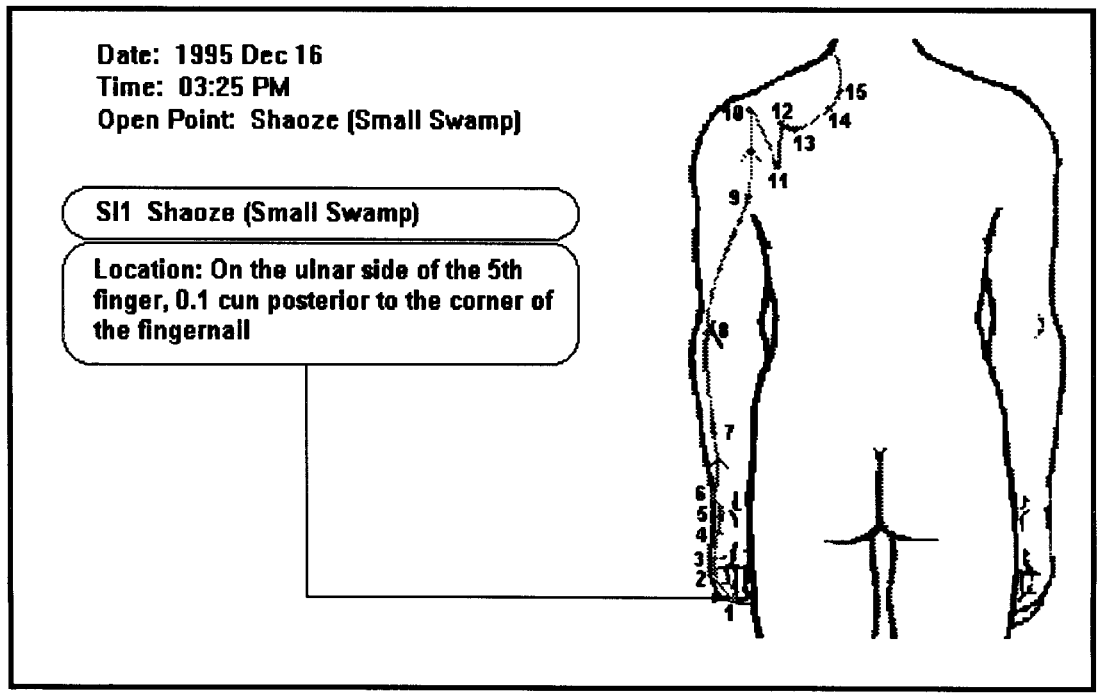
FIG. 4 is a display of a date and time specific biorhythmic acupuncture point.
FIG. 5 is a display of a pictorial description of a name and location of a biorhythmic acupuncture point.

An example display of a date and time specific biorhythmic acupuncture point is depicted in FIG. 4. The particular Gregorian-calendar date and time in FIG. 4 are "1995 DEC 16" and "03:25 PM," noting that the time portion in FIG. 4 does not show seconds. As discussed in the second paragraph of this section, the date "1995 DEC 16" can be converted into a Kan-day 8 and the time "03:25 PM" into a Chih-period 9. As shown in FIG. 3B, the biorhythmic acupuncture point indicated by this Kan-day and Chih-period index is SI-1, which represents the first point on the Small Intestine meridian, and is known as Shaoze (Small Swamp). These findings enable the application program of this embodiment to produce the display shown in FIG. 4, and to update current date and time and their corresponding biorhythmic acupuncture point as long as the application program is kept operating. It is evident that other display arrangements can be made to depict the biorhythmic acupuncture point information presented by the example display shown in FIG. 4.

CONCLUSION, RAMIFICATIONS, AND SCOPE

Thus the reader will see that the preferred embodiment of the invention, described in the preceding section, provides a method for producing an automated display of names of date and time specific biorhythmic acupuncture points. Such an automated display will facilitate the task of identifying biorhythmic acupuncture points, for those interested in the practice of acupuncture or acupressure. An experienced practitioner of acupuncture or acupressure can easily locate an identified biorhythmic acupuncture point on a human subject's skin.

Although the description above contains many specificities, these should not be construed as limiting the scope of the present invention but as merely providing illustrations of a presently preferred embodiment of this invention. Many other variations are possible. For example, another embodiment of the present invention can be described as a method for producing an automated display of textual descriptions of both names and locations of date and time specific biorhythmic acupuncture points. Once the name of a biorhythmic acupuncture point is established, a textual description of a standardized, anatomical location of the acupuncture point can be displayed together with the name so that users of such automated displays can easily locate the acupuncture point without having to memorize its location. The block diagram shown in FIG. 1 can be used to illustrate an electronic apparatus operated by this embodiment of the present invention. The flowchart shown in FIG. 2 can be used to illustrate the operation of this embodiment, provided that a textual description of a location is appended to each of the names of the 120 biorhythmic acupuncture points listed in FIGS. 3A and 3B.

A variation of the preceding embodiment can be described as a method for producing an automated display of pictorial descriptions of both names and locations of date and time specific biorhythmic acupuncture points. This embodiment is a straightforward extension of the preceding embodiment in that its pictorial displays will further simplify the task of users of such automated displays in locating biorhythmic acupuncture points. The block diagram shown in FIG. 1 can be used to illustrate an electronic apparatus operated by this embodiment of the present invention. The flowchart shown in FIG. 2 can be used to illustrate the operation of this embodiment, provided that a pictorial description of a location is appended to each of the names of the 120 biorhythmic acupuncture points listed in FIGS. 3A and 3B. An example display of a pictorial description of a name and location of a biorhythmic acupuncture point is depicted in FIG. 5. Inside the Location box in FIG. 5, the term "cun" is a unit commonly used in the fields of acupuncture and acupressure for measuring distances, and represents a "body inch" which is equivalent to the breadth of the distal phalanx of a human subject's thumb. It is evident that other display arrangements can be made to depict, pictorially, the biorhythmic acupuncture point information presented by the example display shown in FIG. 5, which also depicts a trace of the Small Intestine meridian with fifteen of its acupuncture points labeled as 1 through 15.

Yet another embodiment of the present invention can be described as a method for producing an automated display of names of a set of twelve commonly used time specific biorhythmic acupuncture points. This method can be provided by modifying the preferred embodiment discussed in the preceding section such that it designates a time as the temporal datum, a 24-hour day as the biorhythmic period, and a Chih-period index as the biorhythm-based indexing means. In this embodiment, an information storage means is used to store a list of names of twelve predetermined biorhythmic acupuncture points which are indicated by twelve Chih-period indices. Thus, names of these twelve predetermined acupuncture points can be automatically displayed during their specific Chih-periods of the day.

Accordingly, the scope of the present invention should be determined not by the embodiments and examples illustrated, but by the appended claims and their legal equivalents.

What is claimed is:

1. A method for operating an electronic apparatus, said electronic apparatus comprising a processor means, a time-keeping means, a computation means, an information storage means, a display means, and a monitoring means, said information storage means storing a plurality of predetermined biorhythmic acupuncture point indicators, said method directing said processor means to execute the steps of:

acquiring a temporal datum from said time-keeping means;

executing said computation means to convert said temporal datum into a biorhythm-based indexing means;

using said biorhythm-based indexing means to retrieve a biorhythmic acupuncture point indicator stored in said information storage means;

depicting said biorhythmic acupuncture point indicator on said display means;

depicting said temporal datum on said display means;

executing said monitoring means to acquire a new temporal datum from said time-keeping means at a predetermined frequency, to equate said temporal datum with said new temporal datum, and to convert said temporal datum into a new biorhythm-based indexing means utilizing said computation means; and comparing said biorhythm-based indexing means with said new biorhythm-based indexing means, and, if found identical, branching to said step of depicting said temporal datum; otherwise, equating said biorhythm-based indexing means with said new biorhythm-based indexing means and continuing to said step of using said biorhythm-based indexing means.

2. The method of claim 1, wherein:

said plurality of predetermined biorhythmic acupuncture point indicators is a set of names of 120 predetermined biorhythmic acupuncture points, said temporal datum is a date and time, said step of depicting said temporal datum causing said date and time to be depicted on said display means, said biorhythm-based indexing means is a Kan-day and Chih-period index, said information storage means storing said set of names of 120 predetermined biorhythmic acupuncture points indicated by 120 Kan-day and Chih-period indices, said biorhythmic acupuncture point indicator is a name of a biorhythmic acupuncture point, said step of depicting said biorhythmic acupuncture point indicator causing said name to be depicted on said display means, and said predetermined frequency is once every second.

3. The method of claim 1, wherein:

said plurality of predetermined biorhythmic acupuncture point indicators is a set of textual descriptions of names and locations of 120 predetermined biorhythmic acupuncture points, said temporal datum is a date and time, said step of depicting said temporal datum causing said date and time to be depicted on said display means, said biorhythm-based indexing means is a Kan-day and Chih-period index, said information storage means storing said set of textual descriptions of names and locations of 120 predetermined biorhythmic acupuncture points indicated by 120 Kan-day and Chih-period indices, said biorhythmic acupuncture point indicator is a textual description of a name and location of a biorhythmic acupuncture point, said step of depicting said biorhythmic acupuncture point indicator causing said textual description to be depicted on said display means, and said predetermined frequency is once every second.

4. The method of claim 1, wherein:

said plurality of predetermined biorhythmic acupuncture point indicators is a set of pictorial descriptions of names and locations of 120 predetermined biorhythmic acupuncture points, said temporal datum is a date and time, said step of depicting said temporal datum causing said date and time to be depicted on said display means, said biorhythm-based indexing means is a Kan-day and Chih-period index, said information storage means storing said set of pictorial descriptions of names and locations of 120 predetermined biorhythmic acupuncture points indicated by 120 Kan-day and Chih-period indices, said biorhythmic acupuncture point indicator is a pictorial description of a name and location of a biorhythmic acupuncture point, said step of depicting said biorhythmic acupuncture point indicator causing said pictorial description to be depicted on said display means, and said predetermined frequency is once every second.

5. The method of claim 1, wherein:

said plurality of predetermined biorhythmic acupuncture point indicators is a set of names of twelve predetermined biorhythmic acupuncture points, said temporal datum is a time, said step of depicting said temporal datum causing said time to be depicted on said display means, said biorhythm-based indexing means is a Chih-period index, said information storage means storing said set of names of twelve predetermined biorhythmic acupuncture points indicated by twelve Chih-period indices, said biorhythmic acupuncture point indicator is a name of a biorhythmic acupuncture point, said step of depicting said biorhythmic acupuncture point indicator causing said name to be depicted on said display means, and said predetermined frequency is once every second.

* * * * *